United States Patent [19]

Lin

[11] Patent Number: 5,726,631
[45] Date of Patent: Mar. 10, 1998

[54] STRUCTURE KICK-ACTIVATED WEARABLE ALARM FOR INFANTS

[76] Inventor: Wen-Juei Lin, No. 347, Yuh-Her St., Shin-Diann City, Taipei, Taiwan

[21] Appl. No.: 753,489

[22] Filed: Nov. 26, 1996

[51] Int. Cl.$^6$ ................................................ G08B 23/00
[52] U.S. Cl. .................. 340/573; 340/568; 5/494
[58] Field of Search ........................ 340/573, 539, 340/693, 568; 178/36; 5/494

[56] References Cited

U.S. PATENT DOCUMENTS

| | | | |
|---|---|---|---|
| 4,614,939 | 9/1986 | Wang | 340/573 |
| 4,679,036 | 7/1987 | Cheng | 340/573 |
| 4,846,157 | 7/1989 | Sears | 340/573 |

*Primary Examiner*—Jeffery Hofsass
*Assistant Examiner*—Anh La
*Attorney, Agent, or Firm*—Morton J. Rosenberg; David I. Klein; Jun Y. Lee

[57] ABSTRACT

A kick-activated wearable alarm for infants is provided that includes three temperature sensors and a main controller unit installed in a belt pack. The belt pack is directly worn around the abdominal section of an infant and operates in conjunction with an external receiver, whereby the disclosed structure offers total kicking and fever sensing performance. The belt pack is installed around the abdominal section of an infant with two of the three sensors respectively placed in an exposed state at the anterior and posterior aspects of the abdominal section and the other sensor being placed inside the clothing of the infant. Whether the infant kicks while asleep or awake, or when a fever develops that raises body temperature, the three temperature sensors are connected to a conductor interfaced to the main controller unit. The main controller unit transfers the sensed signal to an external receiver, which emits of an audible alarm. Therefore, in the event of either a situation of kicking or the development of a fever, not only is there immediate notification and alerting, the audible alarm emitted by the receiver does not disturb the slumber of the infant.

6 Claims, 4 Drawing Sheets

STRUCTURE KICK-ACTIVATED WEARABLE ALARM FOR INFANTS

BACKGROUND OF THE INVENTION

Conventional kick-activated wearable alarms for infants are configured somewhat like telephone pagers and mainly consists of temperature sensors, a main control unit, a buzzer and other components, with the entire assembly contained in a box-like enclosure that is suspended on the chest of an infant, such that when the infant is covered with a blanket and kicking occurs, the temperature sensors perform temperature sensing functions and the aforesaid main controller unit initiates the buzzer to emit a sound at the appropriate time, which enables the notification and alerting of the head of the household. However, what cannot be denied about this kind of configuration is that it provides the practical values of being time-sensitive and efficient. Yet, after experiencing usage, people find through utilization that there are a number of disadvantages which await further improvement. For example, since the assembly is entirely contained inside a box-like enclosure, therefore, the physical dimensions of the aforesaid enclosure are relatively large and, furthermore, the thickness thereof cannot be reduced. As such, whenever the infant rolls or repositions itself while asleep, the body of the infant is pressed upon by the box-like enclosure, which results in a loss of comfort. Furthermore, since the aforesaid alarm is suspended in front of the chest, therefore, while the infant is asleep, the entire alarm necessarily presses down on the position covered. As such, in addition to producing discomfort and notably when kicking occurs, the temperature sensors contained inside the aforesaid alarm is precluded from sensing differences in temperature and cannot activate the main controller unit into operation, and thus the actual required functions of the kick-activated alarm expected cannot be accomplished. Furthermore, since the aforesaid buzzer is installed inside the box-like structure and not independently located apart, therefore, if the infant and the head of the family are not sleeping together, and the buzzer emits an audible alarm, the sleeping head of the household often has no means of immediately ascertaining or becoming aware of the onset of a kicking situation and, furthermore, the sound of the aforesaid buzzer causes a direct disturbance to the sleeping infant. Furthermore, when the infant is afflicted by a cold or other illness, which is most worrisome to the head of the household, who has experienced the onset of fever, the aforesaid temperature sensors are inside a box-like enclosure that is suspended anterior to the chest and, furthermore, positioned in between the outside of clothing and the blanket, such that the detection of whether the infant has a fever cannot be provided, which is obviously a disadvantage limiting utilization.

Therefore, as known based on the foregoing explanation, the configuration of the aforesaid kick-activated wearable alarm for infants is manifestly still encumbered by several disadvantages in actual utilization that await further necessary improvements.

SUMMARY OF THE INVENTION

As such, the primary objective of the invention herein is to provide a kind of improved structure kick-activated wearable alarm for infants, wherein the aforesaid main controller unit and the three temperature sensors are contained in a belt pack and, furthermore, after the belt pack is worn around the abdominal section of the infant, one of the aforesaid temperature sensors is positioned inside the clothing of the infant to thereby effectively detect whether the infant has developed a fever with extreme sensitivity, accuracy and efficiency.

Another objective of the invention herein to provide a kind of improved structure kick-activated wearable alarm for infants, wherein after the aforesaid belt pack is worn around the abdominal section of the infant, the other two of the aforesaid three temperature sensors are respectively positioned at the anterior and posterior aspects of the abdominal section, therefore, whether the infant awakes from slumber or repositions its body while asleep, the occurrence of kicking can still be accurately and, furthermore, efficiently detected and warned about.

Yet another objective of the invention herein to provide a kind of improved structure kick-activated wearable alarm for infants, wherein the aforementioned three temperature sensors are connected via a conductor to the main controller unit, and the aforesaid main controller unit by means of a receiver that receives the sense data signal and, furthermore, is caused to emit an audible alarm, and then after the receiver is placed at the side of the person looking after the infant, in the event that kicking or the development of a fever occurs in the infant, not only is there immediate, accurate and verifiable notification and alerting performance, but the invention herein does not disturb the sleeping infant.

Still another objective of the invention herein to provide a kind of improved structure kick-activated wearable alarm for infants, wherein the aforesaid temperature sensors and the main controller unit can be disassembled from, assembled to and separated from the belt pack, which not only effectively facilitates the washing, maintenance and cleanliness of the belt pack, but at the same time effectively provides for simple, convenient and fast assembly.

To enable the examination committee to obtain a further understanding of the objectives, innovations and performance of the invention herein, the brief description of the drawings as well as the detailed description of the invention are provided below.

BRIEF DESCRIPTION OF THE DRAWINGS

FIG. 2A is a perspective drawing of a receiver.

FIG. 3A is a plan view of the main controller unit.

DETAILED DESCRIPTION OF THE INVENTION

Figure 1:
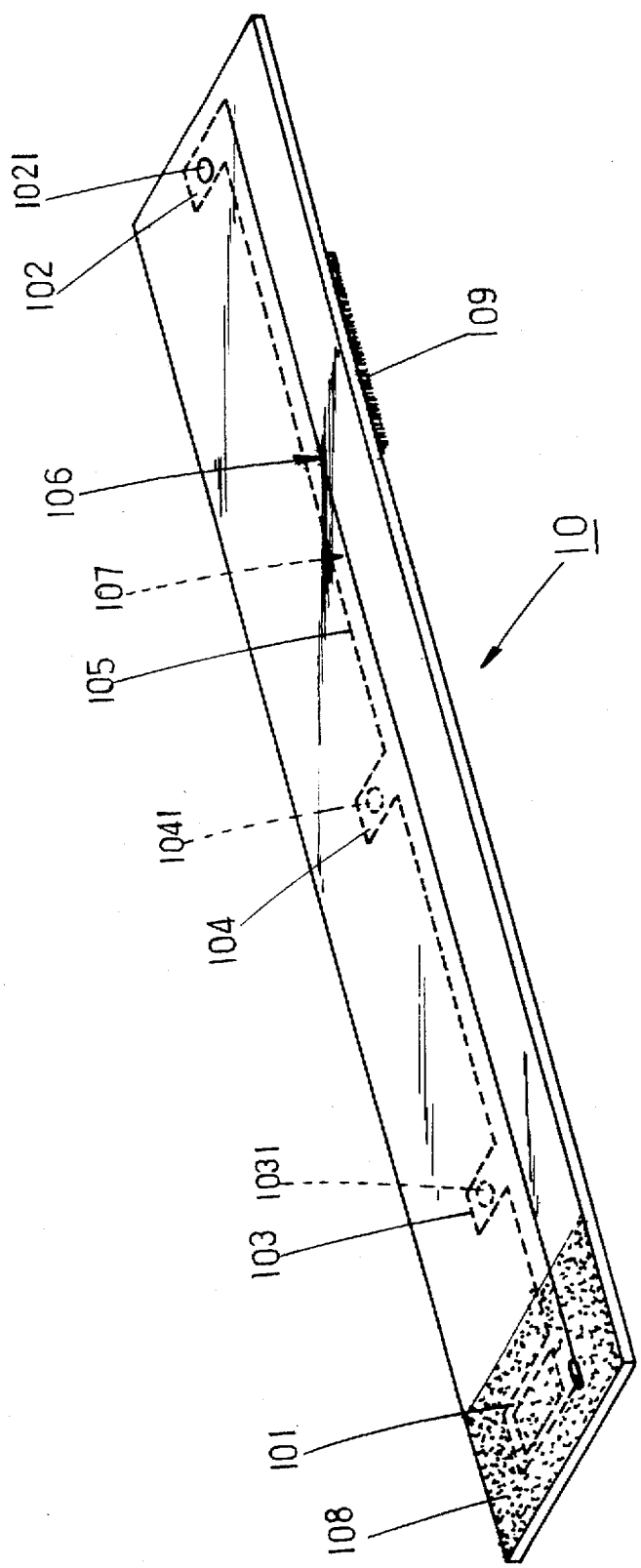
FIG. 1 is an isometric drawing of the belt pack of the invention herein.
Figure 2:
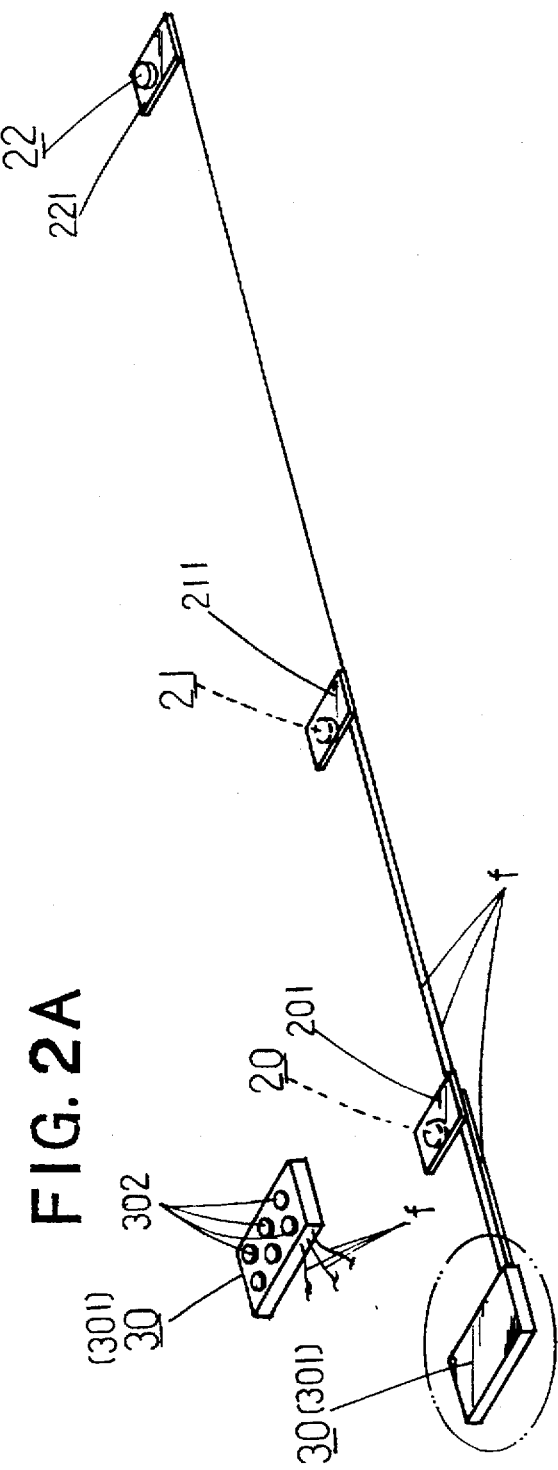
FIG. 2 is an isometric drawing of the three temperature sensors of the main controller unit of the invention herein.
Figure 3:
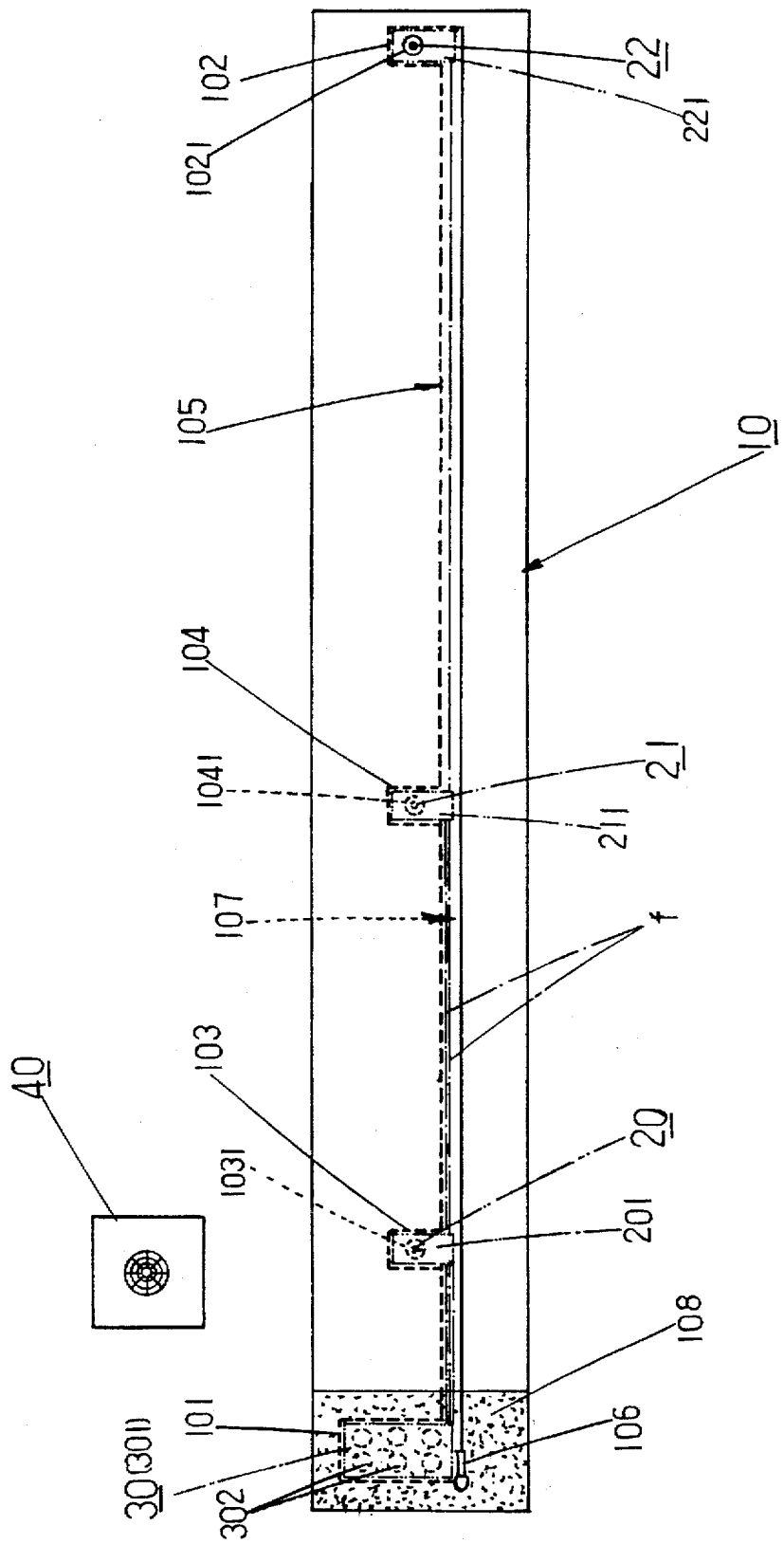
FIG. 3 is an orthographic assembly drawing of the main controller unit, the three temperature sensors and the belt pack of the invention herein from a top perspective.

Referring to FIG. 1, FIG. 2, 2A and FIG. 3, 3A the improved structure infant wear alarm mainly consists of a long belt pack (10) that can be worn lengthwise around the abdomen of an infant, on one side of which and facing lengthwise in the direction of a seam is an oblong recess (101) and on the other side positioned at suitable intervals apart are a total of three small pockets (102), (103) and (104) and in the aforesaid pockets (102), (103) and (104) are the respective through-holes (1021), (1031) and (1041), and in between the aforesaid oblong recess (101) and the front edges of the three pockets (102), (103) and (104), there is a seam having a sealed line (105) installed with an invisible zipper (106), enabling a guide slot (107) to be formed in between, and on the surface at the end of the oblong recess (101), and near the lower surface position of the other end, and positioned in parallel are the fastening strips (108) and (109), of which after being fastened into position around the abdomen of the infant, the aforesaid oblong recess (101) is situated at the lateral aspect of the abdominal section, and the two small pockets (103) and (104) are respectively positioned at the anterior and posterior aspects of the abdominal section and, furthermore, the respective through-holes (1031) and (1041) face outwards and, furthermore, the remaining small pocket (102) is inserted into the clothing of the infant and, furthermore, the through-hole (1021) in the small pocket (102) faces inward; three temperature sensors (20), (21) and (22) that have outer diameters which are no larger than 2 mm and are respectively positioned in the suitable plastic film pieces (201), (211) and (221), and the aforesaid film pieces (201), (211) and (221) are directly contained in the pockets (103), (104) and (102) of the belt pack (10) and, furthermore, allow the temperature sensors (20), (21) and (22) to be exposed at the through-holes (1031), (1041) and (1021) of the pockets (103), (104) and (102), wherein when the aforesaid two temperature sensors (20) and (21) are set to a temperature lower than 28° C. or 26° C., sensing operation is initialized, and the when the other aforesaid temperature sensor (22) is set to a temperature higher than 37.5° C., sensing operation is likewise initialized; a main controller unit (30) that consists of an elongated box (301) (having a thickness of not more than 0.7 cm, a width of not more than 2.5 cm and a length matching the width of the belt pack (10)) that is internally comprised of a number of setting keys (302), an input circuit, a microprocessor (CPU), a wireless triggering circuit and a lithium battery, and a conductor (f) that is connected to the three temperature sensors (20), (21) and (22) and, furthermore, is directly contained in the oblong recess (101) of the belt pack (10), of which the aforesaid setting keys (302) includes a clear key having a reset function to cancel previous settings and, furthermore, cause the circuit to enter the command mode or the standby mode to reduce electric power consumption, a test key utilized for testing the battery and normal circuit operation, and a temperature switch key (i.e., when the two temperature sensors (20) and (21) are normally set to a temperature lower than 28° C. to initialize sensing operation, after the temperature switch key is pressed, the aforesaid set temperature is automatically switched to 26° C.) utilized to switch the temperature settings of the temperature sensors (20) and (21), and a number of time selector keys (includes selector keys for the relatively brief durations of 20 minutes and 30 minutes as well as selector keys for longer durations of one hour, two hours and three hours, such that after pressing the desired selector key, the aforesaid CPU is automatically activated when the period set by the time selector key is reached) utilized to control the microprocessor (CPU) from the standby mode to the active mode and, furthermore, the aforesaid CPU is software controlled and is normally in the standby mode, but when the time selector key is pressed down and, furthermore, after the period set by the aforesaid key is reached, operation commences such that when the two temperature sensors (20) and (21) detect a temperature that is lower than the preset 28° C. or 26° C., or when the other temperature sensor (22) detects a temperature that is higher than 37.5° C., the readings will automatically invoke the generation of electromagnetic waves through the wireless triggering circuit and, furthermore, through the aforesaid conductor (f) positioned in the guide slot (107) of the belt pack (10); a receiver (40) that is independently located at the side of the person looking after the infant and which is internally equipped with an audio circuit and a receiver circuit, and is capable of receiving signals transmitted by the main controller unit (10) and, furthermore, of emitting an audible alarm.

Figure 4:
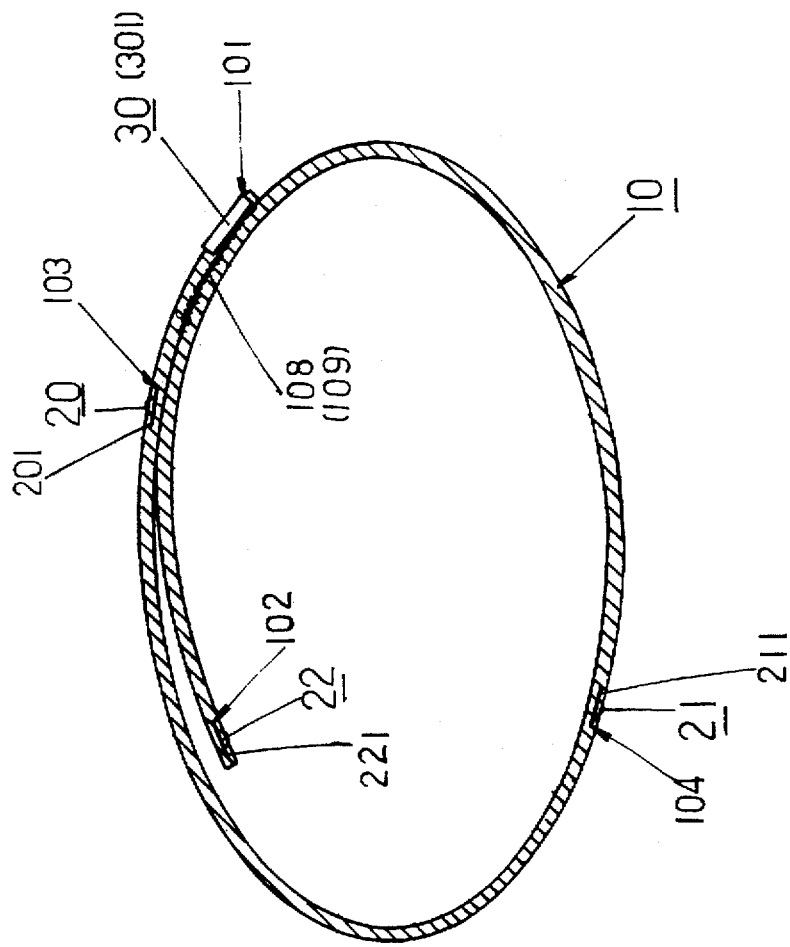
FIG. 4 is an orthographic drawing of the invention here when wrapped around the abdomen of an infant.

Since the aforesaid three temperature sensors (20), (21) and (22) are respectively positioned in the film pieces (201), (211) and (221), therefore, the film pieces (201), (211) and (221) are respectively contained inside the pockets (103), (104), (102) and the oblong recess (101) of the belt pack (10) and, furthermore, such that when the temperature sensors (20), (21) and (22) are exposed via the through-holes (1031), (1041) and (1021) of the pockets (103), (104) and (102), the invisible zipper (105) positioned at the front edge of each pocket (103), (104), (102) and the oblong recess (101) can be pulled into a state of closure and in due course, the aforesaid three temperature sensors (20), (21) and (22) as well as the main controller unit (10) are effectively secured into position and kept from being dislodged or moved; furthermore, as indicated in FIG. 4, when the belt pack (10) is worn on the abdominal section of the infant, since the aforesaid oblong recess (101) is located at the lateral aspect of the abdominal section, therefore, the main controller unit (30) contained inside is obviously prevented from disrupting comfort during periods of repose (actually, since the thickness the aforesaid main controller unit box (301) does not exceed 0.7 cm, therefore, after the belt pack (10) containing the aforesaid box (301) is worn on the abdominal section of the infant, not even the slightest inconvenience or discomfort to the infant occurs) and, at the same time, since the two pockets (103) and (104) of the aforesaid belt pack (10) are situated at the anterior and posterior aspects of the abdominal section, therefore, the aforesaid two temperature sensors (20) and (21) contained inside the aforesaid belt pack (10) and, furthermore, exposed via the through-holes (1031) and (1041) can respectively undertake temperature readings at the exterior lateral aspect of the abdominal section and exterior lateral aspect of the posterior section such that the sensed data as a matter of course, since the film pieces (201) and (211) in which the aforesaid two temperature sensors (20) and (21) are positioned are mounting film pieces that are, furthermore, fabricated of plastic, and the aforesaid temperature sensors (20) and (21) have diameters that do not exceed 2 mm, therefore, the positioning at the abdominal section and the posterior section of the infant does not affect sleeping comfort. Furthermore, since after the aforesaid belt pack (10) is worn around the abdominal section of the infant, the aforesaid temperature sensors (20) and (21) positioned inside the two pockets (103) and (104) of the belt pack (10) can respectively sense temperatures and execute temperature readings at the exterior lateral aspect of the abdominal section and exterior lateral aspect of the posterior section and, furthermore, when the aforesaid two temperature sensors (20) and (21) are preset at a sensing temperature that is lower than 28° C. or 26° C., the temperature sensing operation occurs immediately and, furthermore, the sensed data signal travels directly through the conductor (f) and is transferred to the microprocessor (CPU) of the main controller unit (30) and, therefore, when a person places a blanket on the infant and after the two temperature sensors (20) and (21) of the belt pack (10) are covered, in the event that the child shoves the device by kicking and the aforesaid belt pack (10) become exposed, causing the outside temperature to rapidly decrease and, furthermore, is directly sensed by the temperature sensor (20) or (21), when the aforesaid temperature sensor (20) or (21) senses that the temperature has become lower than the set 28° C. or 26° C., as a matter of course the response operation of the aforesaid temperature sensor (20) or (21) immediately occurs and, furthermore, the data signal is transferred to the microprocessor of the main controller unit (30) and after the aforesaid microprocessor (CPU) receives the data signal, the wireless triggering circuit is enabled to generate electromagnetic waves and, furthermore, the receiver (40) at the side of the person watching over the infant responds by emitting an audible signal, alerting and informing as deemed necessary that the infant has kicked and thereby enabling the invention herein to provide and achieve instantaneous and, furthermore, ensured performance.

In the foregoing description, after the belt pack (10) is worn around the abdominal section of the infant, since the two sensors (20) and (21) are operated through and connected to the conductor (f) and the main controller unit (30) are respectively positioned at the anterior and posterior aspects of the abdominal section, therefore, whether the infant arises or physically turns in a state of slumber, when the blanket covering the body of the infant is shoved by kicking, the temperature sensors have the capability to sense the exposed temperature and as such, can achieve the accurate control of situations wherein the infant has kicked, demonstrating that the utilization objectives and functions expected of the invention herein can be fully achieved, and is ensured to be a genuine improvement over conventional products that are suspended in front of the chest, the usage of which easily results in the disadvantages of inaccurate and imprecise sensing. Of course, as expressed in the foregoing description, since the aforesaid main controller unit (30) is equipped with a switch key to vary the sensing temperature of the two temperature sensors (20) and (21), and the aforesaid two temperature sensors (20) and (21) are normally set to a sensing temperature of 28° C., therefore, when a lower sensing temperature is necessary or desired during utilization, a person only has to directly press the aforesaid switch key, whereupon the sensing temperature of the aforesaid two temperature sensors (20) and (21) are immediately switched to the alternate setting of 26° C., and if it is desired to return to the higher temperature sensing setting of 28° C., then a person only has to directly press the clear key of the main controller unit (30) to automatically achieve the reversion.

Furthermore, since the aforementioned receiver (40) is independently located at the side of the person looking after the infant, therefore, when a data signal of the main controller unit (30) is received and an audible alarm is emitted, not only is the aforesaid person watching the infant effectively informed and alerted, but especially since the emitted alarm sound is not similar to conventional units that produce sound on the body of the infant, the invention herein effectively provides for not awakening the sleeping infant.

Furthermore, after the aforementioned belt pack (10) is worn around the abdominal section of an infant, since the temperature sensor (22) of the pocket (102) positioned at the other side and end of the belt pack (10) is directly inside the clothing of the infant and, furthermore, the sensing temperature is set to the normal human body temperature of 37.5° C. (i.e., when the sensed temperature exceeds 37.5° C., the aforesaid temperature sensor (22) responds by commencing operation), therefore, after the infant is covered by a blanket, the aforesaid human body temperature is directly maintained inside the clothing and dissipation does not easily occur, and as a matter of course, when the infant develops a fever and the body temperature exceeds 37.5° C., the aforesaid temperature sensor (22) located within the clothing is capable of extremely easily and, furthermore, accurately sensing the situation and, furthermore, in a similar manner transfers the sensed data signal through the conductor (f) to main controller unit (30), and the microprocessor of the aforesaid main controller unit (30) causes the wireless triggering circuit to generate electromagnetic waves that reach the receiver (40) at the side of the person watching over the infant, which immediately emits an alerting and informing sound after the reception of the data signal.

Furthermore, the aforementioned main controller unit (30) and receiver (40) are respectively equipped internally with an input circuit, wireless triggering circuit, an audio circuit, a receiver circuit and other componentry based on related principles, and although having similar applications in other electrical designs, no further elaboration is provided in the patent application of the invention herein; however, the other components (such as the microprocessor inside the main controller unit (30), the numerous setting keys and the additional three temperature sensors (20), (21) and (22)) in the configuration and, furthermore, after utilization in the infant kick worn alarm, obviously enable the infant kick worn alarm to provide genuine practical performance that is incomparable with similar products and, therefore, possesses unique usable functions that are innovative in form and progressive.

Furthermore, since the aforementioned three temperature sensors (20), (21) and (22) effect a sensing operation that necessary entails the operational enabling of the microprocessor inside the main controller unit (30) which leads to the emitting of an alarm sound by the receiver (40) as well as control over the aforesaid microprocessor from the standby to the active mode and control via the other time selector keys of the main controller unit (30), therefore, the invention herein has a number of time selector keys and, furthermore, when utilized for different periods of time (such as through the different time selector key settings for 20 minutes, 30 minutes, one hour, two hours or three hours and so on), a person can, according to the physical condition of the infant, select the most appropriate time setting (when the physical condition of the infant is poor, the selector key for a shorter period can be utilized by a person, and after the time set by the aforesaid key is inputted to the microprocessor, automatic operation is enabled, but if the physical condition of the infant is good, then a lengthier period can be chosen by the selector key) to avoid the over-sensing of kicking by the infant that results in the disadvantage of disrupting the sleeping head of the household.

Furthermore, since the conductor (f) in the aforesaid main controller unit (30) and the three temperature sensors (20), (21) and (22), is freely installable on and removable from the belt pack (10), therefore, the aforesaid belt pack (10) can not only be assembled and disassembled for washing to maintain cleanliness, but at the same time, the actual assembly and utilization of the belt pack (10) invention herein is simple, convenient and quick.

What is claimed is:

1. A kick-activated wearable alarm for infants that is mainly comprised of:
 a belt pack that can be worn lengthwise around an abdominal section of an infant, on one side of which and facing lengthwise in a direction of a seam is an oblong recess and on the other side positioned at suitable intervals apart are a total of three small pockets and, furthermore, in said pockets are respective through-holes, and in between said oblong recess and respective front edges of said three pockets, said seam has a sealed line installed with an invisible zipper, enabling a guide slot to be formed in between, and at a surface at an end of said oblong recess near a lower surface position of the other end and positioned in parallel are fastening strips;

three temperature sensors that are respectively positioned in suitable plastic film pieces, and said film pieces are directly contained in said pockets of the belt pack and, furthermore, allow said temperature sensors to be exposed at said through-holes of said pockets;

a main controller unit that consists of an elongated box that is internally comprised of a number of setting keys, an input circuit, a microprocessor (CPU), a wireless triggering circuit and a lithium battery, and a conductor that is connected to said three temperature sensors and, furthermore, is directly contained in said oblong recess of said belt-shaped pack; and, a receiver that is independently located at a side of a person looking after the infant and which is internally equipped with an audio circuit and a receiver circuit, and is capable of receiving signals transmitted by said main controller unit and, furthermore, of emitting an audible alarm.

2. The kick-activated wearable alarm for infants as recited in claim 1 wherein, when said belt pack is worn on the abdominal section of the infant, said oblong recess containing said main controller unit is positioned at a lateral aspect of the abdominal section, two of said temperature sensors that are inside two of said pockets at two ends of said belt pack are respectively positioned at an anterior of the abdominal section and a posterior section thereof, and said temperature sensor in said pocket positioned at the other side and end of said belt pack is positioned inside the clothing of the infant.

3. The kick-activated wearable alarm for infants as recited in claim 2 wherein, the sensing temperature of said two temperature sensors that are positioned at the anterior and posterior aspects of the abdominal section of the infant is set to a temperature lower than 28° C. or 26° C. to enable the detection of kicking, and the sensing temperature of the other of said three temperature sensors, positioned inside the clothing of the infant, is set to a temperature higher than 37.5° C. to enable the detection of fever, with the corresponding sensed signal data is transferred through said conductor to the microprocessor of said main controller unit.

4. The kick-activated wearable alarm for infants as recited in claim 3 wherein, said main controller unit is internally equipped with said number of setting keys, including a clear key to cancel various settings and enable entry into a command mode or a standby mode, a test key utilized for circuit and battery testing and a switch key utilized to switch the kick-activation temperature settings of said two temperature sensors as well as to control said microprocessor from the standby mode, and a number of time selector keys for enabling different time settings.

5. The kick-activated wearable alarm for infants as recited in claim 4 wherein, said microprocessor in said main controller unit is normally in the standby mode, and automatically enters an active mode after a time period set by said time selector keys is reached and, furthermore, when data signals of said three temperature sensors are received, said wireless triggering circuit is directly caused to generate a signal to said receiver.

6. The kick-activated wearable alarm for infants as recited in claim 1 wherein, after said main controller unit and said three temperature sensors are respectively contained inside said oblong recess, wherein two of said pockets of said belt pack and said conductor are installed in said guide slot of said belt pack, said belt pack being sealed into a state of closure by pulling said invisible zipper such that said components are effectively secured into position and kept from being dislodged or moved.

* * * * *